United States Patent
Prasad

(10) Patent No.: US 10,588,885 B2
(45) Date of Patent: Mar. 17, 2020

(54) CHLOROGENIC ACID COMPOSITION AND METHOD FOR ITS USE IN THE TREATMENT OF ALZHEIMER'S DISEASE

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 0 days.

(21) Appl. No.: 15/647,192

(22) Filed: Jul. 11, 2017

(65) Prior Publication Data

US 2018/0028482 A1 Feb. 1, 2018

Related U.S. Application Data

(60) Provisional application No. 62/361,491, filed on Jul. 12, 2016.

(51) Int. Cl.
*A61K 31/216* (2006.01)
*A61K 9/00* (2006.01)
*A61K 36/28* (2006.01)

(52) U.S. Cl.
CPC .......... *A61K 31/216* (2013.01); *A61K 9/0053* (2013.01); *A61K 36/28* (2013.01)

(58) Field of Classification Search
None
See application file for complete search history.

(56) References Cited

U.S. PATENT DOCUMENTS

| | | | |
|---|---|---|---|
| 2011/0223281 A1 | 9/2011 | Ibarra et al. | |
| 2011/0313014 A1* | 12/2011 | Robert | A23F 5/14 514/419 |
| 2014/0314727 A1* | 10/2014 | Singh | C11B 1/10 424/93.21 |

OTHER PUBLICATIONS

Gray "Caffeoylquinic acids in Centella asiatica protect against β-amyloid toxicity" J alz dis 40(2):359-373 (Year: 2014).*
Kwon "Neuroprotective effects of chlorogenic acid on scopolamine-induced amnesia via anti-acetylcholinesterase and anti-oxidative activities in mice" Euro J pharma 649:210-217 (Year: 2010).*
Stark "Isolation, Structure Determination, Synthesis, and Sensory Activity of N-Phenylpropenoyl-L-amino Acids from Cocoa (*Theobroma cacao*)" J agric Food Chem 53:5419-5428 (Year: 2005).*
Reitz "Toward precision medicine in Alzheimer's disease" Ann Trans Med 4(6):107 (Year: 2016).*
Stanford "Alzheimer's Prevention, Treatment and Research—A Q&A with Dr. Frank Longo" stanfordhealthcare.org/stanford-health-now/2016/alzheimers-prevention-treatment-research-qa-longo.html accessed on May 3, 2016 (Year: 2016).*
Weisz "Identification and quantification of phenolic compounds from sunflower (*Helianthus annuus*L.) kernels and shells by HPLC-DAD/ESI-MS" food chem 115:758-765 (Year: 2009).*
Farah (in Coffee: Emerging Health Effects and Disease Prevention, First Edition. Edited by Yi-Fang Chu., 2012 John Wiley & Sons, Inc. Published 2012 by Blackwell Publishing Ltd).
Murase et al. Am J Physiol Endocrinol Metab 300: E122-E133, 2011.
Venkatesh et al., J. Pharm. Sci. 89, 145-54 (2000).
Monteiro The Journal of Nutrition, Journal of Nutrition (2007), 137(10), 2196-2201.
Meng et al.; Roles of Chlorogenic Acid on Regulating Glucose and Lipids Metabolism: A Review, Evidence-Based Complementary and Alternative Medicine, vol. 2013, Article ID 801457, pp. 1-11 (2013).
Weisz et al. ("Identification and quantification of phenolic compounds from sunflower (*Helianthus annuus*L.) kernels and shells by HPLC-DAD/ESI-MSn," Food chemistry, vol. 115, No. 2, pp. 758-765 (2009)).

* cited by examiner

*Primary Examiner* — Adam Weidner
(74) *Attorney, Agent, or Firm* — TMB Law

(57) ABSTRACT

The invention provides compositions comprising chlorogenic acid and methods for their use and manufacture in the treatment of Alzheimer's disease. The compositions can be formulated from botanical sources of chlorogenic acid including sunflower seed extract.

13 Claims, 10 Drawing Sheets

CHLOROGENIC ACID COMPOSITION AND METHOD FOR ITS USE IN THE TREATMENT OF ALZHEIMER'S DISEASE

CROSS-REFERENCE TO RELATED APPLICATIONS

This application claims the benefit of provisional application No. 62/361,491 filed Jul. 12, 2016, the entire contents of which are incorporated herein by reference for all purposes.

FIELD OF THE INVENTION

The invention relates to botanical formulations, including methods of making and using botanical formulations in therapeutic applications. More particularly, the invention relates to botanical formulations comprising chlorogenic acids and methods for their use and manufacture in the treatment and prevention of Alzheimer's disease.

BACKGROUND OF THE INVENTION

Alzheimer's disease is a neurodegenerative disease and one of the most common forms of dementia. Diminished cholinergic functioning, a biomarker of normal aging, is especially severe in cases involving dementia. In Alzheimer's disease, amyloid plaque deposits in key components of the cholinergic system cause a drastic decline in acetylcholine levels. To make matters worse, already reduced acetylcholine levels continue to be degraded by acetylcholinesterase, further impairing memory and eroding cognitive ability. Further, the production of reactive oxygen species plays a key role in Alzheimer's disease pathology leading to neuronal dysfunction and cell death.

Tau proteins, mostly found in neurons of the central nervous system, have an important role in stabilizing microtubules, critical structures responsible for various movements in cells. If Tau is hyperphosphorylated, it loses effectiveness in stabilizing microtubules and starts to aggregate. Hyperphosphorylation and aggregation of Tau is observed in dementias like Alzheimer's disease.

What is needed in the art is a therapeutic agent that can act on multiple targets of Alzheimer's disease pathology. It is believed that therapeutic interventions that could postpone the onset and progression of Alzheimer's disease would dramatically reduce the disease prevalence. Natural botanical formulations offer an attractive alternative to the therapeutic intervention of Alzheimer's disease.

SUMMARY OF THE INVENTION

The present invention provides compositions of chlorogenic acid and methods for their use and manufacture in the treatment of Alzheimer's disease. The compositions provide a natural therapeutic agent that addresses multiple targets of Alzheimer's disease pathology simultaneously.

Thus, it is an object of the invention to provide a method for treating Alzheimer's disease comprising administering to a patient in need thereof a composition comprising chlorogenic acid.

In some embodiments, the composition comprises at least one of 3-Caffeoylquinic acid (3-CQA), 5-Caffeoylquinic acid (5-CQA), 4-Caffeoylquinic acid (4-CQA), 3,4-Dicaffeoylquinic acid (3,4-DiCQA), 3,5-Dicaffeoylquinic acid (3,5-DiCQA), and 4,5-Dicaffeoylquinic acid (4,5-DiCQA).

In some embodiments, the composition comprises 3-Caffeoylquinic acid (3-CQA), 5-Caffeoylquinic acid (5-CQA), 4-Caffeoylquinic acid (4-CQA), 3,4-Dicaffeoylquinic acid (3,4-DiCQA), 3,5-Dicaffeoylquinic acid (3,5-DiCQA), and 4,5-Dicaffeoylquinic acid (4,5-DiCQA).

In some embodiments, the composition comprises, by weight, 4.1±1.42% 3-Caffeoylquinic acid (3-CQA), 28±4.65% 5-Caffeoylquinic acid (5-CQA), 6.5±2.25% 4-Caffeoylquinic acid (4-CQA), 0.84±0.26% 3,4-Dicaffeoylquinic acid (3,4-DiCQA), 1.23±0.34% 3,5-Dicaffeoylquinic acid (3,5-DiCQA), and 1.85±0.42% 4,5-Dicaffeoylquinic acid (4,5-DiCQA).

In some embodiments, the composition is substantially free of any other chlorogenic acid.

In some embodiments, the composition has a total chlorogenic acid content of 42.5±2.5% chlorogenic acid by weight.

DEFINITIONS

Figure 1:
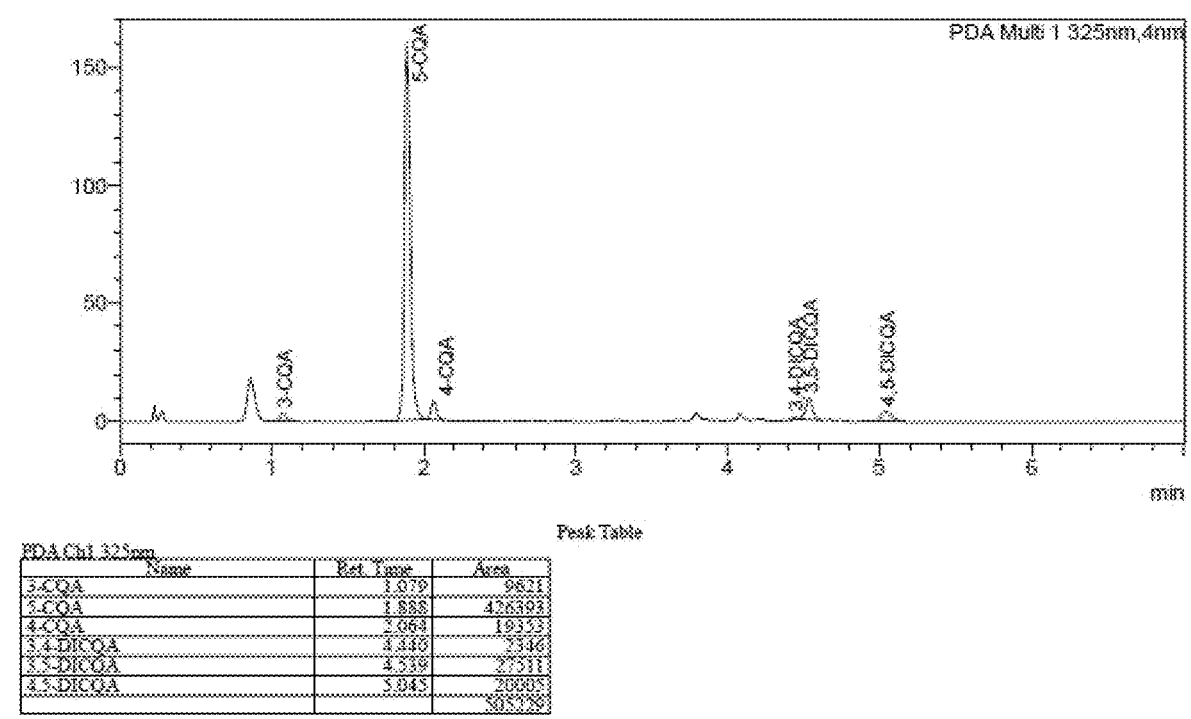
FIG. 1 shows an HPLC chromatogram of sunflower seed chlorogenic acids.
Figure 2:
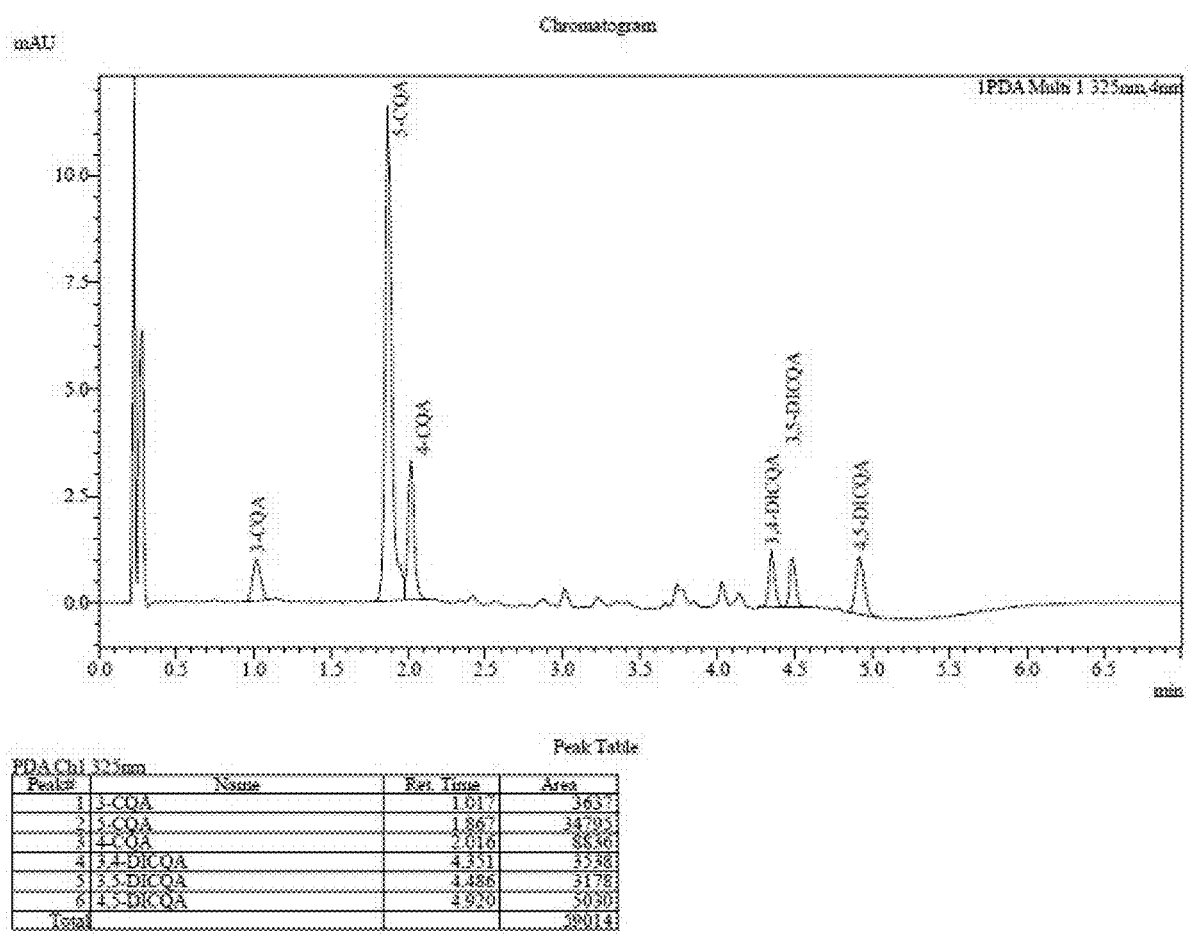
FIG. 2 is an HPLC chromatogram showing the chlorogenic acids present in an embodiment of the inventive composition.
Figure 3:
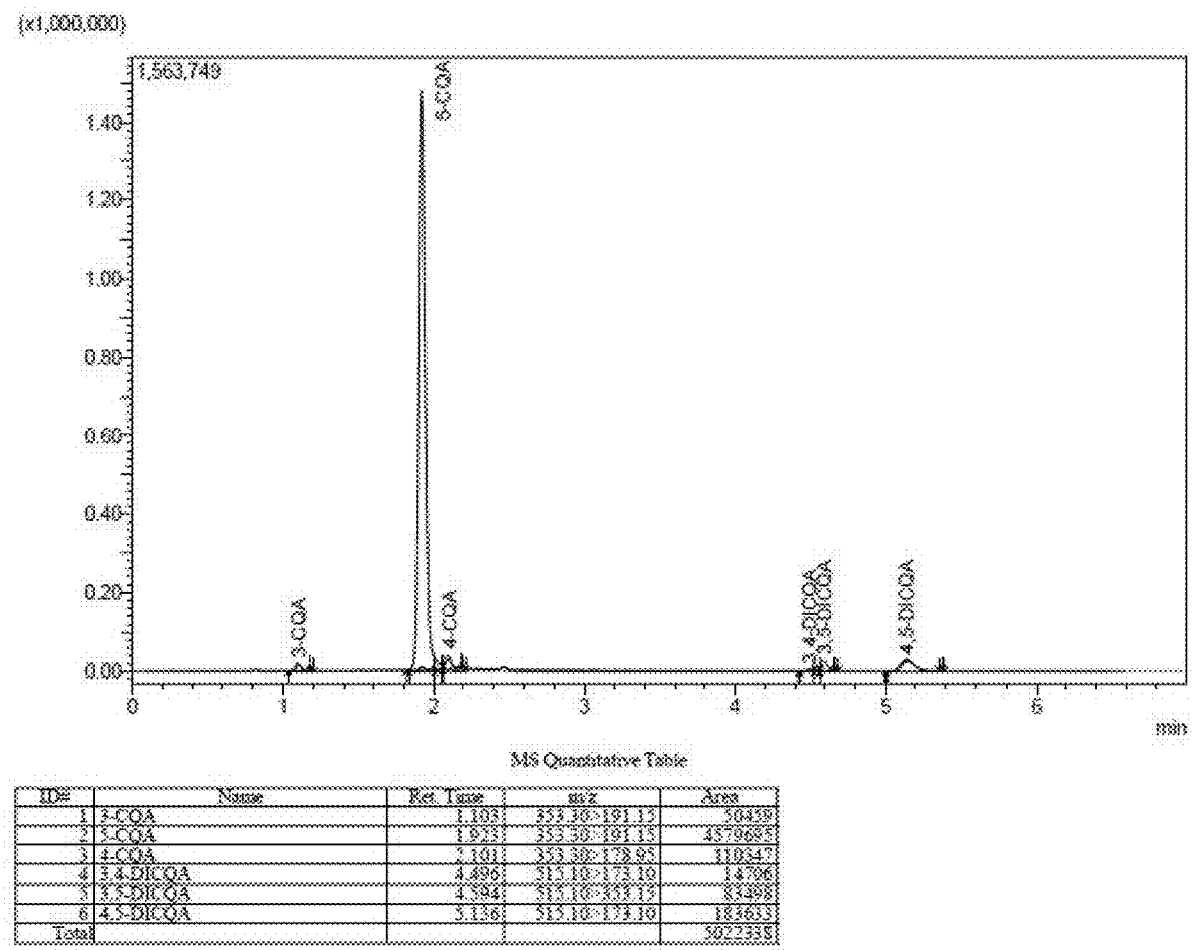
FIG. 3 is an LCMS/MS chromatogram of sunflower seed.
Figure 4:
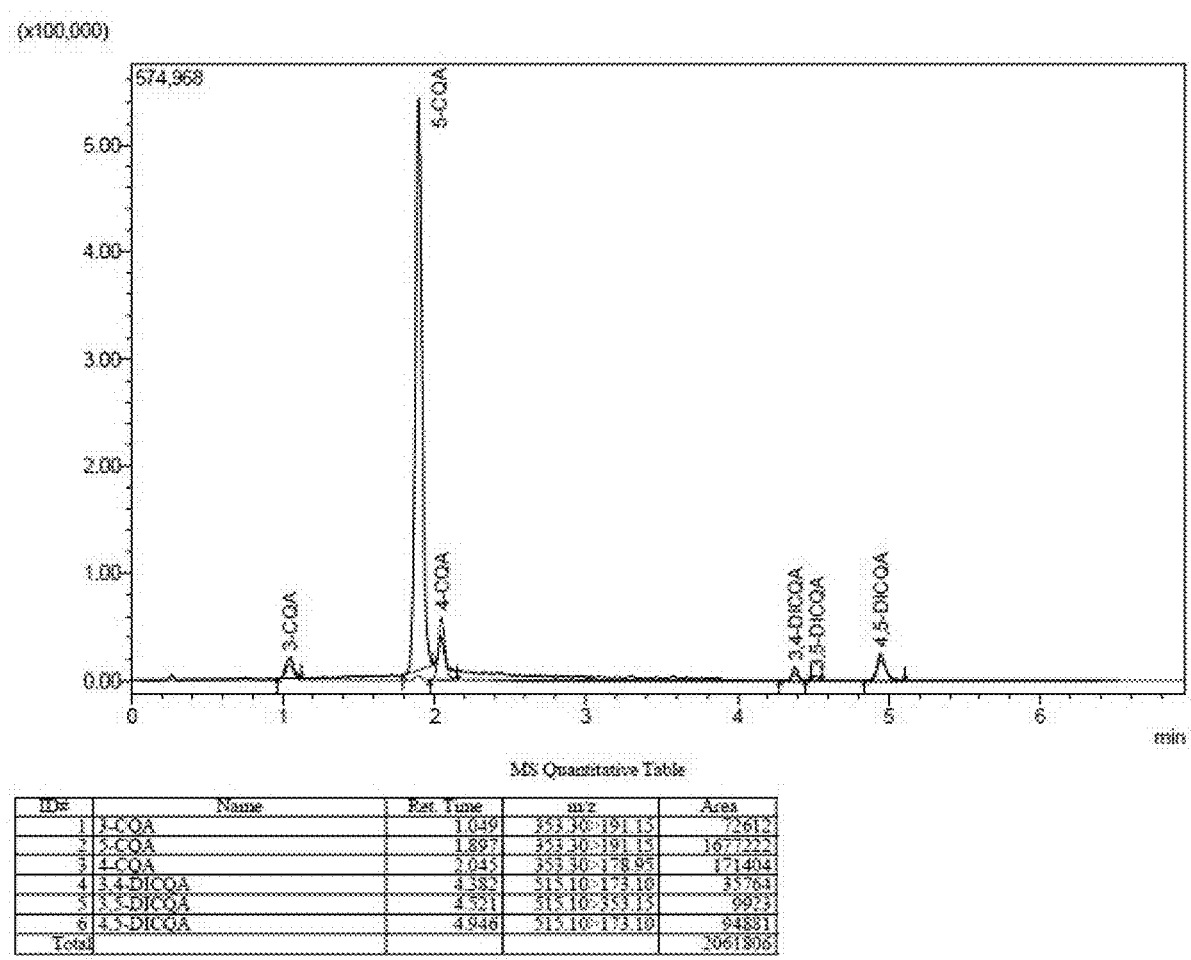
FIG. 4 is an LCMS/MS chromatogram showing the chlorogenic acids present in an embodiment of the inventive composition.

The term "about" means greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values.

The phrase "chlorogenic acids" is a generic term which collectively refers to monocaffeoylquinic acids including 3-caffeoylquinic acid, 4-caffeoylquinic acid and 5-caffeoylquinic acid; monoferuloylquinic acid including 3-feruloylquinic acid, 4-feruloylquinic acid and 5-feruloylquinic acid; and dicaffeoylquinic acid including 3,4-dicaffeoylquinic acid, 3,5-dicaffeoylquinic acid and 4,5-dicaffeoylquinic acid.

The term "increase," or "enhance," refers to any measurable increase in a target parameter that results from a given set of conditions relative to the absence of such conditions.

The terms "purified" and "isolated" refer to a substance that is at least 75%, 85%, 90%, 95%, 100% free of any other substance, including any percentage that intervenes such specifically listed percentages.

The phrase "pharmaceutically acceptable carrier" refers to an ingredient in a pharmaceutical formulation, other than an active ingredient, which is nontoxic to a subject. Pharmaceutically acceptable carriers include, but are not limited to, buffers, excipients, stabilizers, and preservatives.

The term "reduce," or "decrease," refers to any measurable decrease in a target parameter that results from a given set of conditions relative to the absence of such conditions.

The terms "subject" and "patient" are used interchangeably herein to refer to an individual that receives the administration of an agent, including but not limited to the compositions of the invention, in the treatment of a targeted condition, disease or disorder. Subjects include, but are not limited to, mammals such as humans and livestock (e.g. sheep, cattle, horses, goats, pigs, and poultry), for example. Subjects include, but are not limited to, animals used in scientific research (e.g. mice, rats, rabbits, and guinea pigs), humans in clinical trials, and individuals once used as controls.

The phrase "substantially free" means that the substance to which it refers is either completely absent or present in an insignificant amount such that the substance does not have any effect in the environment or biological system in which the substance is introduced. Substantially free can include a value that is less than 1 w/w %.

The term "treatment" (and grammatical variations thereof such as "treat" or "treating") refers to clinical intervention in an attempt to alter the natural course of a targeted disease, disorder or condition in the subject being treated. Desirable effects of treatment include, but are not limited to, alleviation or amelioration of one or more symptoms, diminishment of or delay in the appearance of or worsening of any direct or indirect pathological consequences of the targeted disease, decrease of the rate of the targeted disease's progression, and amelioration or palliation of the targeted disease state.

The phrase "early Alzheimer's disease" refers patients with mild cognitive impairment, such as a memory deficit, due to Alzheimer's disease and subjects having Alzheimer's disease biomarkers, for example amyloid positive patients.

The phrase "mild Alzheimer's disease" refers to a stage of Alzheimer's disease characterized by an MMSE score of 20 to 26.

The phrase "mild to moderate Alzheimer's disease" encompasses both mild and moderate Alzheimer's disease characterized by an MMSE score of 18 to 26.

The phrase "moderate Alzheimer's Disease" refers to a stage of Alzheimer's disease characterized by an MMSE score of 18 to 19.

The phrase "severe or late-stage Alzheimer's disease" refers to very severe cognitive decline when individuals lose the ability to respond to their environment, the ability to speak and, ultimately, the ability to control movement.

The term "late-onset Alzheimer's disease" refers to Alzheimer's disease which has a time of onset after the subject reaches 40 years of age.

DETAILED DESCRIPTION OF THE INVENTION

The present invention provides compositions comprising chlorogenic acid and methods for making and using such compositions in the treatment of Alzheimer's disease.

In at least one embodiment, the invention provides a composition comprising one or more chlorogenic acids. The chlorogenic acids can include, but are not limited to, 3-O-caffeoylquinic acid (3 CQA), 4-O-caffeoylquinic acid (4 CQA), 5-O-caffeoylquinic acid (5 CQA), 5-O-feruloylquinic acid, 3,4-O-dicaffeoylquinic acid (3,4 Di CQA), 3,5-O-dicaffeoylquinic acid (3,5 Di CQA), 4,5-O-dicaffeoylquinic acid (4,5 Di CQA), and combinations thereof. The composition can comprise 3 CQA, 5 CQA, 4 CQA, 3,4 Di CQA, 3,5 Di CQA, and 4,5 Di CQA. The composition can comprise one or more chlorogenic acids, wherein the chlorogenic acids are selected from the group consisting of 3 CQA, 5 CQA, 4 CQA, 3,4 Di CQA, 3,5 Di CQA, and 4,5 Di CQA. The composition can comprise a mixture of chlorogenic acids consisting of 3 CQA, 5 CQA, 4 CQA, 3,4 Di CQA, 3,5 Di CQA, and 4,5 Di CQA. The composition can comprise a mixture of two or more chlorogenic acids, wherein the chlorogenic acids are selected from the group consisting of 3 CQA, 5 CQA, 4 CQA, 3,4 Di CQA, 3,5 Di CQA, and 4,5 Di CQA. The composition can comprise any combination of the chlorogenic acids disclosed herein, wherein one or more individual chlorogenic acid is specifically excluded. For example, the composition can be substantially free of one or more of 3-caffeoylquinic acid, 4-caffeoylquinic acid and 5-caffeoylquinic acid; monoferuloylquinic acid including 3-feruloylquinic acid, 4-feruloylquinic acid and 5-feruloylquinic acid; and dicaffeoylquinic acid including 3,4-dicaffeoylquinic acid, 3,5-dicaffeoylquinic acid and 4,5-dicaffeoylquinic acid. The composition can be substantially free of monoferuloylquinic acids. The composition can be substantially free of one or more of 3-feruloylquinic acid, 4-feruloylquinic acid and 5-feruloylquinic acid.

The composition can be formulated to attain a desired total chlorogenic acid content. As used herein, the phrases "total chlorogenic acid content" and "total chlorogenic acid" refer to the sum of the chlorogenic acids that are present in the composition. The total chlorogenic acid content of the composition can be between about 20-100 w/w %. The composition can comprise one or more chlorogenic acids, wherein the total chlorogenic acid content of the composition, is 20 w/w %, 21 w/w %, 22 w/w %, 23 w/w %, 24 w/w %, 25 w/w %, 26 w/w %, 27 w/w %, 28 w/w %, 29 w/w %, 30 w/w %, 31 w/w %, 32 w/w %, 33 w/w %, 34 w/w %, 35 w/w %, 36 w/w %, 37 w/w %, 38 w/w %, 39 w/w %, 40 w/w %, 41 w/w %, 42 w/w %, 43 w/w %, 44 w/w %, 45 w/w %, 46 w/w %, 47 w/w %, 48 w/w %, 49 w/w %, 50 w/w %, 51 w/w %, 52 w/w %, 53 w/w %, 54 w/w %, 55 w/w %, 56 w/w %, 57 w/w %, 58 w/w %, 59 w/w %, 60 w/w %, 70 w/w %, 80 w/w %, 90 w/w % or 100 w/w %, as well as any amount intervening these specifically described amounts. The total chlorogenic acid content can be about 42 w/w %. The total chlorogenic acid content can be 42.5±2.5 w/w %.

Specific ranges for the amount of individual chlorogenic acids that are present in the composition are within the scope of the invention. For example, the composition can comprise about 1-15 w/w % 3 CQA, about 5-50 w/w % 5 CQA, about 1-20 w/w % 4 CQA, about 0.5-10 w/w % 3,4 Di CQA, about 0.5-10 w/w % 3,5 Di CQA, and about 0.5-10 w/w % 4,5 Di CQA, wherein the amounts of the individual chlorogenic acids are adjusted to achieve a total chlorogenic acid content that is 100 w/w % or less relative to the other constituents in the composition. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the total chlorogenic acid content of the composition is 42.5±2.5 w/w %. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the composition is substantially free of other any other chlorogenic acid. The composition can comprise a mixture of chlorogenic acids consisting of 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The composition can comprise a mixture of chlorogenic acids consisting of about 4 w/w % 3CQA, about 28 w/w % 5 CQA, about 7 w/w % 4 CQA, about 1 w/w % 3,4 Di CQA, about 1 w/w % 3,5 Di CQA, and about 2 w/w % 4,5 Di CQA. The composition can comprise about 4 w/w % 3CQA, about 28 w/w % 5 CQA, about 7 w/w % 4 CQA, about 1 w/w % 3,4 Di CQA, about 1 w/w % 3,5 Di CQA, and about 2 w/w % 4,5 Di CQA, wherein the composition is substantially free of any other chlorogenic acid. It will be understood that all amounts of chlorogenic acids referenced in the present disclosure, including total chlorogenic acid content, can be obtained by any suitable method available to one skilled in the art. Such methods include, but are not limited to, HPLC and the Folin-Ciocalteus method.

In some aspects of the invention, the composition comprises a mixture of chlorogenic acids, wherein the individual chlorogenic acids are present in a desired ratio. The ratio of the chlorogenic acids can be derived from any weight to weight percentage disclosed herein. For example, a composition comprising 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA can provide a composition comprising said chlorogenic acids in a ratio of 4.9:33.3:7.7:1.0:1.5:2.2, by weight. Thus, the composition can comprise 3 CQA, 5 CQA, 4 CQA, 3,4 Di CQA, 3,5 Di CQA, and 4,5 Di CQA in a ratio of about 4.9:33.3:7.7:1.0:1.5:2.2, by weight. The composition can comprise 3 CQA, 5 CQA, 4 CQA, 3,4 Di CQA, 3,5 Di CQA, and 4,5 Di CQA in a ratio of about 5:33:8:1:1:2, by weight. The composition can comprise 3 CQA, 5 CQA, 4 CQA, 3,4 Di CQA, 3,5 Di CQA, and 4,5 Di CQA in a ratio of about 4:28:7:1:1:2, by weight. The compositions expressed as a ratio herein can further comprise another component in addition to the chlorogenic acids. Such components include, but are not limited to, pharmaceutically acceptable carriers, excipients, flavourings, sweeteners, vitamins, minerals, amino acids, proteins, peptides, enzymes, bulking agents, binding agents, emulsifiers, oils (e.g. comestible oils such as peanut oil, coconut oil, safflower oil, sunflower oil, canola oil, olive oil, vegetable oil, corn oil, and the like), lecithins, starches, pectins, sugars, preservatives, colourings, pharmaceuticals (e.g. small molecules), antibodies, natural and synthetic hormones, or a combination thereof.

In some aspects, the invention provides a method for making a composition comprising chlorogenic acids. Such methods can be practiced using one or more commercially available purified (e.g. reagent grade) chlorogenic acids. The method can comprise providing two or more purified chlorogenic acids, and combining the chlorogenic acids to achieve the mixtures of chlorogenic acids, and their relative amounts, as described herein. For example, the composition can be made by combining purified chlorogenic acids to provide a composition comprising 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The composition can be made by combining purified chlorogenic acids to provide a composition comprising 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the composition is substantially free of any other chlorogenic acids. The composition can be made by combining purified chlorogenic acids to provide a composition comprising a mixture of chlorogenic acids consisting of 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The composition can be made by combining purified chlorogenic acids to provide a composition comprising 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the composition has a total chlorogenic acid content of 42.5±2.5 w/w %.

Methods for making the inventive composition can be practiced with chlorogenic acids obtained from any botanical source that contains the chlorogenic acids that are desired for use in the composition. The botanical source of chlorogenic acids can be sunflower (*Helianthus annus*). The chlorogenic acids can be formulated from any sunflower material capable of providing the desired chlorogenic acids. The sunflower material can be fresh or dried. The composition can be formulated from sunflower seeds (e.g. green seeds, or dried or powdered seeds), leaves, stems, stalks, flowers, pollen, roots, or a combination thereof. In some aspects, the composition is formulated from sunflower seeds. In other aspects, the composition is formulated from sunflower seed powder. The botanical source of chlorogenic acids can be green coffee beans. In some aspects of the invention, chlorogenic acids are derived from the botanical source by extraction. One skilled in the art will appreciate that the chlorogenic acids can be extracted from the botanical source using any suitable extraction method. Suitable solvents for extracting the chlorogenic acids include, but are not limited to, polar solvents (e.g. protic and aprotic), non-polar solvents, supercritical fluids, and the like. Suitable protic solvents include, but are not limited to, acetic acid, methanol and ethanol. Suitable aprotic solvents include, but are not limited to, ethyl acetate and tetrahydrofuran. The solvent can be water, including, but not limited to, demineralized water, reverse osmosis water, distilled water, or a combination thereof. In some aspects, solvent extraction is combined with cation exchange chromatography to achieve enhanced purification of the chlorogenic acids desired for the compositions described herein. Suitable methods for extracting chlorogenic acids are described in the following publications, the entire disclosures of which are incorporated herein by reference for all purposes: U.S. Pat. Nos. 8,309,150; 9,029,588; 9,301,939; and US 20150231103.

Some aspects of the invention concern formulating the composition for administration to a subject. Accordingly, the compositions of the invention can be formulated to be administered orally, sublingually, intranasally, topically, intravenously, intramuscularly, subcutaneously, subdermally, buccally, parenterally, intravaginally, rectally, and by inhalation. The composition can be in a dosage form that includes, but is not limited to, a powder, pill, tablet, pellet, capsule, thin film, solution, spray, syrup, linctus, lozenge, pastille, chewing gum, paste, vapour, suspension, solution, emulsion, ointment, cream, lotion, liniment, gel, drop, topical patch, buccal patch, bead, gummy, gel, sol, injection, and the like. The composition can comprise at least one pharmaceutically acceptable carrier. Suitable carriers for use with the invention include, but are not limited to, those disclosed in Remington's Pharmaceutical Sciences, 18th ed. the disclosure of which is incorporated herein by reference in its entirety for all purposes. The pharmaceutically acceptable carrier can be an artificial pharmaceutical carrier. The composition can be formulated to achieve a timed release. The composition can be formulated with enteric coatings, or encapsulated, such as by liposomes or micelles, for example.

In some aspects of the invention, the composition comprises one or more other components. Such components include, but are not limited to, flavourings, sweeteners, vitamins, minerals, amino acids, proteins, peptides, enzymes, bulking agents, binding agents, emulsifiers, oils (e.g. comestible oils such as peanut oil, coconut oil, safflower oil, sunflower oil, canola oil, olive oil, vegetable oil, corn oil, and the like), lecithins, starches, pectins, sugars, preservatives, colourings, pharmaceuticals (e.g. small molecules), antibodies, natural and synthetic hormones, and the like.

In at least one aspect, the invention provides a method for treating Alzheimer's disease in a subject in need thereof comprising administering to the subject a composition comprising chlorogenic acid, wherein administering the composition to the subject treats Alzheimer's disease in the subject. The composition can comprise one of more of the compositions described herein. The composition can comprise 3 CQA, 5 CQA, 4 CQA, 3,4 Di CQA, 3,5 Di CQA, and 4,5 Di CQA. The composition can comprise one or more chlorogenic acids selected from the group consisting of 3 CQA, 5 CQA, 4 CQA, 3,4 Di CQA, 3,5 Di CQA, and 4,5 Di CQA. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the composition is substantially free of any other chlorogenic acid. The composition can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the total chlorogenic acid content of the composition is 42.5±2.5 w/w %. The composition can comprise a mixture of two or more chlorogenic acids, wherein the chlorogenic acids are selected from the group consisting of 3 CQA, 5 CQA, 4 CQA, 3,4 Di CQA, 3,5 Di CQA, and 4,5 Di CQA. The composition can comprise a mixture of chlorogenic acids consisting of 3 CQA, 5 CQA, 4 CQA, 3,4 Di CQA, 3,5 Di CQA, and 4,5 Di CQA. The composition can comprise chlorogenic acids derived from a botanical source. The composition can comprise chlorogenic acids derived from sunflower seed. The composition can comprise an extract of sunflower seed.

In some aspects of the invention, the invention provides a method for treating Alzheimer's disease in a subject in need thereof comprising administering to the subject a composition comprising an extract of sunflower seed, wherein the extract comprises 3 CQA, 5 CQA, 4 CQA, 3,4 Di CQA, 3,5 Di CQA, and 4,5 Di CQA. The extract can comprise a mixture of chlorogenic acids consisting of 3 CQA, 5 CQA, 4 CQA, 3,4 Di CQA, 3,5 Di CQA, and 4,5 Di CQA. The extract can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA. The extract can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the total chlorogenic acid content of the composition is 42.5±2.5 w/w %. The extract can comprise 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA, wherein the extract is substantially free of any other chlorogenic acids.

The method of the invention can be practiced by administering the composition according to any administration route capable of providing a therapeutic effect in the subject. Suitable administration routes include, but are not limited to orally, topically, buccally, sub-lingually, parenterally, intravenously, intraarterially, subdermally, subcutaneously, ocularly, intravaginally, rectally, by inhalation, or a combination thereof. The composition can be administered as a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, or injection.

The composition can be administered at a dose of between about 5 mg/day to about 500 mg/day. The composition can be administered at a dose between about 20 mg/day to about 1 g/day. The composition of the invention can be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition can be administered at a dosage of between about 400 mg/day to about 500 mg/day, between about 300 mg/day to about 400 mg/day, between about 200 mg/day to about 300 mg/day, between about 100 mg/day to about 200 mg/day, between about 100 mg/day to about 200 mg/day, or about 20 mg/day to about 100 mg/day. It is contemplated that the composition can be administered at any dosage that intervenes the dosages called out in this specification. The composition can be administered at 200 mg/day for 14 days. The composition can be administered at 400 mg/day for 14 days.

The composition can be administered at a dose that is determined by the body weight of the subject. The dose can be about 5 mg/kg to about 500 mg/kg. The composition can be administered at a dose of about 20 mg/kg, about 21 mg/kg, about 22 mg/kg, about 23 mg/kg, about 24 mg/kg, about 25 mg/kg, about 26 mg/kg, about 27 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 40 mg/kg, about 45 mg/kg, about 50 mg/kg, about 100 mg/kg, about 150 mg/kg, about 200 mg/kg, about 250 mg/kg, about 300 mg/kg, about 350 mg/kg, about 400 mg/kg, about 450 mg/kg, or about 500 mg/kg, as well as any dosage intervening these specifically disclosed amounts. The composition can be administered at a dosage of between about 400 mg/kg to about 500 mg/kg, about 300 mg/kg to about 400 mg/kg, about 200 mg/kg to about 300 mg/kg, about 100 mg/kg to about 200 mg/kg, about 100 mg/kg to about 200 mg/kg, or about 20 mg/kg to about 100 mg/kg. It is contemplated that the composition can be administered at any dosage that intervenes the dosages called out in this specification. The dosages by body weight disclosed herein can be administered one, two, three, four, five, six, seven, eight or more times per day. The composition can be administered at 200 mg/kg per day for 14 days. The composition can be administered at 400 mg/kg per day for 14 days.

In at least one embodiment, the invention provides a method for preventing Alzheimer's disease in a subject in need thereof, wherein the method comprises administering to the subject the composition described herein. The method can prevent Alzheimer's disease in a subject at risk of developing Alzheimer's disease. The method can prevent Alzheimer's disease in a subject that is pre-symptomatic for Alzheimer's disease.

The subject can have early Alzheimer's disease. The subject can have mild Alzheimer's disease. The subject can have mild to moderate Alzheimer's disease. The subject can have moderate Alzheimer's disease. The subject can have severe or late-stage Alzheimer's disease. The subject can have early onset or late-onset Alzheimer's disease. The subject can have cerebral amyloidosis. Treating subjects for Alzheimer's disease as disclosed herein can alleviate or ameliorate one or more symptoms of Alzheimer's disease. Treating subjects for Alzheimer's disease as disclosed herein can diminish or delay in the appearance of or worsening of any direct or indirect pathological consequences of Alzheimer's disease. Treating subjects for Alzheimer's disease as disclosed herein can decrease the rate of the progression of Alzheimer's disease in the subject. In some aspects, the method of the invention treats one or more symptoms of Alzheimer's disease. Symptoms can include, but are not limited to, memory deficits, impaired cognition, dementia and impaired speech. The method of the invention can alleviate or ameliorate one or more symptoms, diminish or delay the appearance of or worsening of symptoms, and/or decrease the rate of the progression of symptoms.

Without being limited to any particular theory or mechanism, administering the composition to the subject treats Alzheimer's disease by imparting one or more therapeutic effects in the brain tissue of the subject. Such therapeutic effects include, but are not limited to: inhibiting Tau phosphorylation; inhibiting the formation of beta amyloid plaques; inhibiting the formation of neurofibrillary tangles; inhibiting acetylcholinesterase activity; inhibiting reductions in GSH levels; increasing glutathione (GSH) levels; inhibiting reductions in superoxide dismutase (SOD) activity; increasing SOD activity; inhibiting beta secretase; and inhibiting lipid peroxidation. Administering the composition can restore GSH levels to normal. Administering the composition can restore Tau phosphorylation levels to normal. Administering the composition can restore acetylcholinesterase activity to normal.

In at least one embodiment, the composition of the invention finds use in a variety of therapeutic and preventive applications. In some embodiments, the composition is administered to a subject for preventing oxidation and the production of free radicals in the subject (i.e. antioxidant activity). Thus, the composition can have a nutritive effect for maintaining and promoting health in a subject.

The present disclosure is further described in the light of the following non-limiting examples which are set forth for illustration purpose only and not to be construed for limiting the scope of the disclosure.

EXAMPLES

Example 1 exemplifies an embodiment of the composition of the invention and method of making thereof. Example 2 exemplifies the analytical examination of a composition of the invention. Example 3 exemplifies the antioxidant and acetylcholinesterase activities of a composition of the invention in vitro. Example 4 exemplifies the use of a composition of the invention in the prevention of dementia using experimental animals. Example 5 exemplifies the use of a composition of the invention in the inhibition of acetylcholinesterase and beta secratase using in silico docking studies.

Example 1

This example describes the preparation of one embodiment of the composition. The processes described in this example can be scaled up to produce larger quantities of the composition. The details provided for preparation of the following composition reflect the presently preferred method for extract preparations and should not be considered as limiting. The quantities and times described below can be varied substantially to provide suitable formulations derived from sunflower seed in accordance with the invention.

Preparation of Composition 100 kg of sunflower seed powder (20-40 mesh) was taken into a clean vertical 1.0 kL extractor. The bottom of the extractor comprised a perforated plate on which filtration cloth was fixed. The bottom of the extractor was connected to a transfer pump, input and outputs of the transfer pump connected to a T bend. One end was connected to the extractor top for circulation of the extraction mass during the extraction period and other end of the T bend was connected to a receiver tank.

The above mentioned mass was extracted with 7-8 bed volumes of demineralised water. Extraction was continued at 80-85° C. temperature about 7-8 hrs with continuous circulation of extract with transfer pump. After completion of extraction, the extract was filtered through a 5 micron SS candle filter and clear extract collected in a receiver tank. The bed was re-extracted by adding 5-6 bed volumes of demineralised water 3 more times at 80-85° C. temperature about 7-8 hrs and filter through 5 micron SS candle filter. All the extracts were collected in a receiver tank and the combined extract concentrated in a reactor under vacuum at 80-85° C. till extract TDS reach 25-30 w/v % and cooled to room temperature. The oily layer was separated and an aqueous layer of 40-50 L was collected.

The pH of the above aqueous layer was adjusted to 2-2.2 with dilute inorganic acid ($H_2SO_4$, HCl or $H_3PO_4$) and stirred well about 15 minutes. The solution was filtered through a celite bed to make it into clear solution. The filtrate was loaded into a macroreticular polymeric adsorption (Amberlite XAD-16N, XAD-16, XAD-7, and XAD-4 Made by Rohm & Haas Company) resin column at the rate of 2-3 bed volumes/hour. The resin bed was washed with 4-6 bed volumes of demineralised water at the rate of 2-3 bed volumes/hour and eluted with 3-4 bed volumes of 70-80 v/v % aliphatic alcohol preferably ethyl alcohol at the rate of 2-3 bed volumes/hour. The eluent in the reactor was concentrated at 75-80° C. under reduced pressure until free from ethyl alcohol. The resulting mass was dissolved into demineralised water until the TDS reached 25-30 w/v %. The solution pH was made up to 4.5-4.6 by adding dilute sodium bicarbonate solution in order to get a clear solution. The extract was spray dried at 210±5° C. Yield of the extract was about 2.8±0.2 w/w %.

Properties of the Inventive Composition

Total polyphenols by Folin-Ciocalteus method measured 47.5±2.5 w/w %.

Total chlorogenic acids by HPLC analysis measured 42.5±2.5 w/w %.

Chlorogenic acid content of the composition is described in Table 1.

TABLE 1

Chlorogenic acids composition of an embodiment of the inventive composition

| Molecule | Quantity (w/w %) |
|---|---|
| 3-Caffeoylquinic acid (3-CQA) | 4.1 ± 1.42 |
| 5-Caffeoylquinic acid (5-CQA) | 28 ± 4.65 |
| 4-Caffeoylquinic acid (4-CQA) | 6.5 ± 2.25 |
| 3,4-Dicaffeoylquinic acid (3,4-DiCQA) | 0.84 ± 0.26 |
| 3,5-Dicaffeoylquinic acid (3,5-DiCQA) | 1.23 ± 0.34 |
| 4,5-Dicaffeoylquinic acid (4,5-DiCQA) | 1.85 ± 0.42 |

Content of Sunflower Seed Extract

Total polyphenols by Folin-Cioucalteus method measured 1.8±0.4 w/w %.

Total chlorogenic acids by HPLC analysis method measured 1.65±0.25 w/w %.

Chlorogenic acid composition of sunflower seed is tabulated as below (Table 2).

TABLE 2

Chlorogenic acid content of sunflower seeds

| Molecule | Quantity (w/w %) |
|---|---|
| 3-Caffeoylquinic acid (3-CQA) | 0.04 ± 0.02 |
| 5-Caffeoylquinic acid (5-CQA) | 1.35 ± 0.25 |
| 4-Caffeoylquinic acid (4-CQA) | 0.08 ± 0.04 |
| 3,4-Dicaffeoylquinic acid (3,4-DiCQA) | 0.0068 ± 0.0001 |
| 3,5-Dicaffeoylquinic acid (3,5-DiCQA) | 0.1 ± 0.04 |
| 4,5-Dicaffeoylquinic acid (4,5-DiCQA) | 0.08 ± 0.02 |

All references to the "composition," "the inventive composition," and "SUN-CA" in the following examples and their results shall refer to the composition prepared according to Example 1, unless expressly stated otherwise.

Example 2

This example describes the phytochemical analysis of the composition from Example 1.

Estimation of Total Polyphenolic Content in the Composition by Folin-Ciocalteu's Method Preparation of Standard Curve:

100 mg of standard chlorogenic acid (98% pure) was dissolved in 100 mL of 50% methanol solution (1 mg/mL) and then further diluted to 30, 60, 90, 120, 150 and 180 µg/mL. 1 mL aliquot of each dilution was taken in a test tube and diluted with 10 mL of distilled water. Then 1.5 mL Folin Ciocalteu's reagent was added and allowed to incubate at room temperature for 5 minutes. Four mL of 20% (w/w) $Na_2CO_3$ was added in each test tube, adjusted with distilled water up to the mark of 25 mL, agitated and left to stand for 30 min at room temperature. Absorbance of the standard was measured at 755 nm using UV/VIS spectrophotometer (Schimadzu, Japan) against blank (distilled water).

Sample Preparation 15-20 mg of the composition was taken into 100 mL of volumetric flask, then added to about 50 mL of 50% methanol solution and sonicated for 5 minutes. The volume was made up to 100 mL with 50% methanol. 5.0 mL of the above solution was further diluted to 10 mL using 50% methanol.

Procedure 15 mL of the 50% methanol solution was taken into a series of test tubes. To this 1 mL of Folin-Ciocalteu reagent was added followed by 1 mL of sample solution. The reaction mixture was allowed to incubate at room temperature for 5 minutes. Four mL of 20% (w/w) $Na_2CO_3$ was added in each test tube, adjusted with distilled water up to the mark of 25 mL, agitated and left to stand for 30 min at room temperature. Absorbance of the standard was measured at 755 nm using UV/VIS spectrophotometer (Schimadzu, Japan) against blank (distilled water). The percentage of total polyphenols was determined as below:

$$\% \text{ Total polyphenols} = \frac{\frac{A_{sample} - b}{m} \times V \times DF \times 100}{W_{sample} \times 1000}$$

Where, V—original volume (50 mL), W—sample weight in grams, DF—Dilution factor, $A_{sample}$—Sample absorbance, m,b—Coefficients of standard curve slope and y-intercept Determination of Total Chlorogenic Acids in Sunflower Seed and the Composition by HPLC Analysis Analytical Parameters Column: XB-C18 100 A, 2.6 µm, 50×2.1 mm Phenomenex. (Kinetex)
Pump: Nexera X2, LC-30AD Shimadzu
Detector: SPD-M20A PDA
Wave length: 325 nm
Flow rate: 0.6 mL/min
Volume of injection: 1 µL
Run time: 7 min
Mobile phase: 0.1% Formic acid in HPLC grade water: Acetonitrile
Reference standard: Chlorogenic acid sigma standard—98%
Gradient:

| Time | Concentration (Acetonitrile) |
|------|------------------------------|
| 0.01 | 5 |
| 4.0 | 20 |
| 5.0 | 5 |
| 7.0 | Stop |

Standard Preparation 15-20 mg of standard chlorogenic acid (98%) was weighed accurately into 50 ml standard flask, added to 30 ml 70% methanol (LCMS grade) and sonicated about 10 minutes. The volume was made up to the mark with same solvent. 10 mL of the above solution was pipetted to 50 mL standard flask and made up to the mark with same solvent and sonicated about 10 minutes.

Sample Preparation 40-50 mg of sample was weighed accurately into 50 ml standard flask, added 30 ml 70% methanol (LCMS grade) and sonicated about 10 minutes. The volume was made up to the mark with same solvent. 10 mL of the above solution was pipetted to 50 mL standard flask and made up to the mark with same solvent and sonicated about 10 minutes.

Raw Material Sample Preparation 1000-1500 mg of raw material powder was weighed accurately into 100 mL RB flask, added 40 mL 70% methanol. The mixture was refluxed about 30 minutes and cooled to room temperature followed by filtration in a 100 mL standard flask. The extraction was repeated twice with 30 mL of 70% methanol and filtered. The solution was made up to 100 mL using 70% methanol and sonicated about 10 minutes.

Calculation:

$$\% \text{ of Chlorogenic acids} = \frac{\text{Peak area of the sample} \times \text{Conc. of the } STD \times \text{purity of the } STD}{\text{Peak area of the standard} \times \text{Conc. of the sample}}$$

Analytical Parameters

Column: XB-C18 Phenomenex (Kinetex), 100 A, 2.6 µm & 50×2.1 mm
Pump: Nexera X2, LC-30AD Shimadzu
Detector: SPD-M20A PDA and LCMS/MS 8040
Wave length: 325 nm
Flow rate: 0.6 mL/min
Volume of injection: 1 µL
Run time: 7 min.
Mobile phase (A:B): 0.1% Formic acid in LCMS grade water:Acetonitrile
DL Temp.: 300° C.
Nebulizing gas flow: 3 L/min.
Heat block temp: 400° C.
Drying gas flow: 15 L/min.
MS detection: ESI-ve mode, SIM at m/z 353 and 515, MRM at m/z
   191, 178 and 353
Gradient:

| Time | B concentration (Acetonitrile) |
|------|--------------------------------|
| 0.01 | 5 |
| 4.0 | 20 |
| 5.0 | 5 |
| 7.0 | Stop |

Sample Preparation 40-50 mg of sample was weighed accurately into 50 mL standard flask, added 30 mL 70% methanol (LCMS grade) and sonicated about 10 minutes. Volume was made up to the mark with the same solvent. 10 mL of the above solution was pipetted into 50 mL standard flask and make up to the mark with same solvent and sonicated about 10 minutes.

Raw Material Sample Preparation 1000-1500 mg of raw material powder was weighed accurately into 100 mL RB flask, added 40 mL 70% methanol (LCMS grade). The mixture was refluxed about 30 minutes and cooled to room temperature followed by filtration in a 100 mL standard flask. The extraction was repeated twice with 30 mL of 70% methanol and filtered. The solution was made up to 100 mL using 70% methanol and sonicated about 10 minutes.

Example 3

This example relates the use of the inventive composition for antioxidant and acetylcholinesterase activities in vitro.

The sample was prepared in 10% dimethyl sulphoxide (1 mg/mL) and further diluted to 10, 20, 40, 60, 80 and 100 µg/mL for the in vitro studies.

In Vitro Antioxidant Studies

Determination of 2,2-Diphenyl-1-Picrylhydrazyl (DPPH) Radical Scavenging Assay

The free radical scavenging capacity of the inventive composition was determined using DPPH scavenging assay (Braca et al. 2001). DPPH solution was prepared in 95% methanol. Freshly prepared DPPH solution was taken in test tubes and different concentration of test samples were added and incubated for 20 min. The absorbance was read at 517 nm using a spectrophotometer. Blank was prepared containing the same volume of reaction mixture without any test sample. The percentage of scavenging was calculated using following formula:

$$\% \text{ Scavenging} = A_c - A_s/A_c \times 100$$

Where $A_C$ was the absorbance of the control (blank) and $A_s$ was the absorbance in the presence of the composition.

Figure 5:
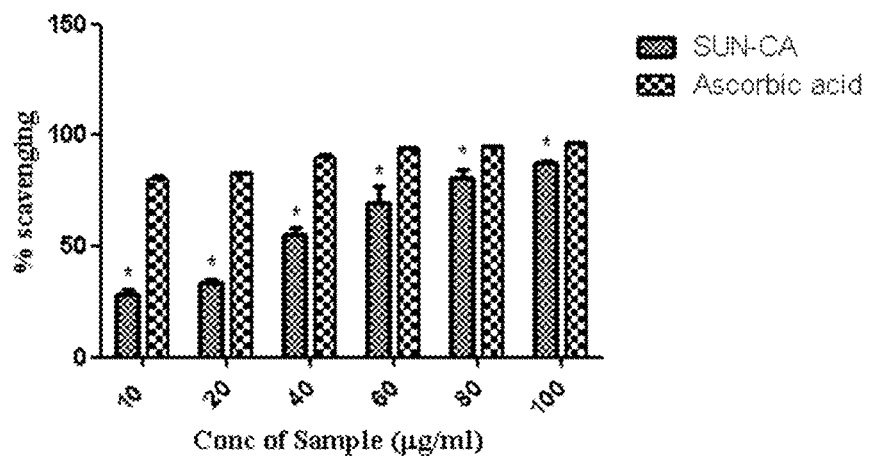
FIG. 5 shows DPPH scavenging by an embodiment of the inventive composition (10 µg-100 µg/mL). The values are mean±SEM. The data were significant at $p<0.0001$ compared to ascorbic acid.

The results set out in FIG. 5 below demonstrate strong free radical scavenging of the inventive composition in a concentration dependent manner. The percentage scavenging was 87.35±0.53 at 100 µg/mL concentration of the composition. The data were highly significant compared to standard ascorbic acid ($p<0.0001$). The IC50 value of the composition was determined to be 38.49 µg/mL.

Determination of Acetylcholinesterase Activity

Inhibition of acetylcholinesterase activity was measured using a 96-well microplate reader (Thermo Scientific Multiscan EX) based on Ellman's method (Ellman et al. 1961). In the 96-well plates, a reaction mixture of 25 µl of 15 mM acetylthiocholine iodide in water, 125 µl of 3 mM DTNB and 25 µl of different concentrations of the composition were added, and the absorbance was measured at 405 nm. Thereafter, 25 µl of AChE solution (0.22 U/ml) was added to the wells and the microplate was read again at the same wavelength 10 times with 1 min intervals. Galanthamine dissolved in methanol was used as standard drug at 1 mg/ml concentrations; a blank of methanol in 50 mM Tris-HCl, (pH 8) was used. The percentage inhibition for each test solution was then calculated using the following equation:

$$\text{Inhibition } (\%) = 1 - (A_{sample}/A_{control}) \times 100$$

Where $A_{sample}$ is the absorbance of the sample and $A_{control}$ is the absorbance of the blank.

Estimation of IC50 Values

The IC50 values (concentration of test compounds that inhibits the hydrolysis of substrates by 50%) were determined by spectrophotometric measurement of the effect of increasing concentrations of test compounds (the composition and positive control) on enzyme activity. To calculate the IC50 values, each sample was assayed at five concentrations (100, 80, 40, 20, 10 µg/ml). IC50 values were obtained from dose-effect curves by linear regression.

Figure 6:
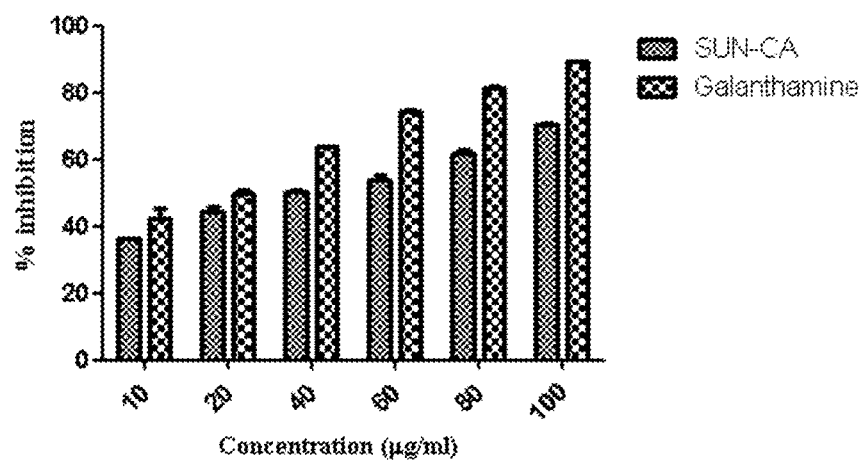
FIG. 6 shows in vitro acetylcholinesterase inhibition by an embodiment of the inventive composition. The values are mean±SEM. The data were significant at $p<0.0001$ compared to ascorbic acid.

The inhibition effect of the composition was clearly evident from this in vitro assay (FIG. 6). The results were comparable to the standard galanthamine and found significant at $p<0.001$. The composition exhibited profound inhibitory activity with an IC50 value 43 µg/mL. At 100 g/mL concentration, the composition showed appreciable effect with a percentage inhibition of 70.24±0.82.

Example 4

This example relates to the use of the composition in the prevention of dementia such as Alzheimer's disease using experimental animals. The composition was evaluated for the neuroprotection in scopolamine-induced dementia including the parameters such as determination of acetylcholinesterase inhibition and antioxidant enzyme activities, quantification of Tau hyperphosphorylation in brain.

Animals: Albino mice
Gender: Male
No of animals: 40
Housing: 6/cage, 12 hrs light/dark cycle
Temperature: 25±2° C.

Scopolamine-Induced Dementia in Mice

Scopolamine induced Alzheimer's type dementia model has been widely used to provide a pharmacological model of memory dysfunction for screening potential cognition enhancing agents. The cognitive-enhancing activity of the composition on scopolamine induced memory impairments in rats was investigated by using behavioural and biochemical parameters.

Experimental Design

Male Albino mice divided into six groups with eight animals in each group. The experimental design for the evaluation of the composition is detailed in Table 3.

TABLE 3

Experimental design for the evaluation of cognitive function in mice

| Groups | Treatment | Dose | No. of animals |
|---|---|---|---|
| Group I | Control | 10 ml/kg vehicle p.o. | 8 |
| Group II | Scopolamine 0.5 mg/kg, i.p | 10 ml/kg vehicle p.o. | 8 |
| Group III | Donepezil + Scopolamine 0.5 mg/kg, i.p | 5 mg/kg p.o. | 8 |
| Group IV | Composition + Scopolamine 0.5 mg/kg, i.p | 200 mg/kg p.o. | 8 |
| Group V | Composition + Scopolamine 0.5 mg/kg, i.p | 400 mg/kg p.o. | 8 |

Experimental model: An elevated plus-maze consisting of two open and two enclosed arms was employed for an evaluation of cognition improvement upon treatment with the composition in mice.

The study parameters included transfer latency, inhibition of acetylcholineterase activity, antioxidant enzyme activities and Tau protein hyperphosphorylation.

Elevated Plus Maze Test

The plus-maze was made of plywood and consisted of two open arms (21.5×7.5 cm) and two enclosed arms (21.5×7.5×20 cm) which extended from a central 7.5×7.5 cm platform. The plus-maze was elevated 38 cm above the floor. The enclosed arms were painted black. The procedure of the test was similar to that described by Itoh et al. (1990). On the 1st day (training) a mouse was placed at the end of one open arm, facing away from the central platform. The latency for the mouse to move from the open to one of the enclosed arms was recorded. Following entry into the arm the animals were allowed to explore the apparatus for 30 s. Twenty-four hours later, the second trial (retention test) was performed. The drugs were administered immediately after the 1st training day, i.e., soon after the mouse was removed from the maze. After behavioural testing, mice were sacrificed and their hippocampi were removed for biochemical assays.

Figure 7:
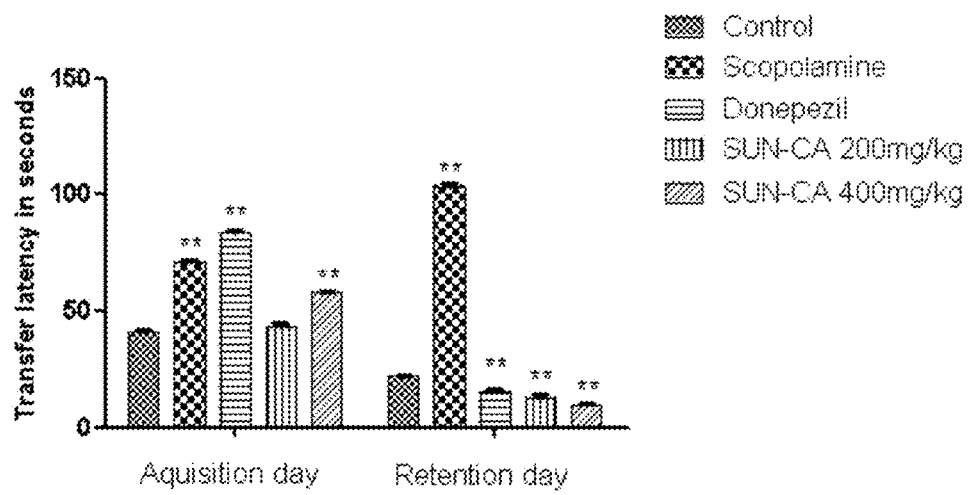
FIG. 7 shows the effect of an embodiment of the inventive composition on transfer latencies of mice in an elevated plus maze. The values are mean±SEM (n=8). The data were analyzed using two way ANOVA. **$p<0.001$ compared to normal control

Transfer latency (TL) on the first day ($14^{th}$ day of treatment) reflected acquisition of learning behaviour of mice while TL on next day reflected retention of memory. The composition was administered for 14 days and had significant effect ($p<0.001$) on TL on the $14^{th}$ and $15^{th}$ day in elevated plus maze test (FIG. 7). Treatment with the composition showed remarkable reduction ($p<0.001$) in TL on retention day ($15^{th}$ day), indicating significant improvement in learning and memory. The results were comparable to standard Donepezil.

Determination of Acetylcholinesterase (AchE) Activity

The mice were decapitated; brains removed quickly and placed in ice-cold saline. Frontal cortex, hippocampus and septum (and any other regions of interest) were quickly dissected out on a petri dish chilled on crushed ice. The tissues were weighed and homogenized in 0.1M Phosphate buffer (pH 8). 0.4 ml aliquot of the homogenate was added to a cuvette containing 2.6 mL phosphate buffer (0.1M, pH 8) and 100 µL of DTNB. The contents of the cuvette were mixed thoroughly by bubbling air and absorbance measured at 412 nm in a spectrophotometer. When absorbance reached a stable value, it was recorded as the basal reading. 20 µL of substrate i.e., acetylthiocholine iodide was added and changes in absorbance were recorded for a period of 10 minutes at intervals of 2 minutes. Change in the absorbance per minute was determined.

Figure 8:
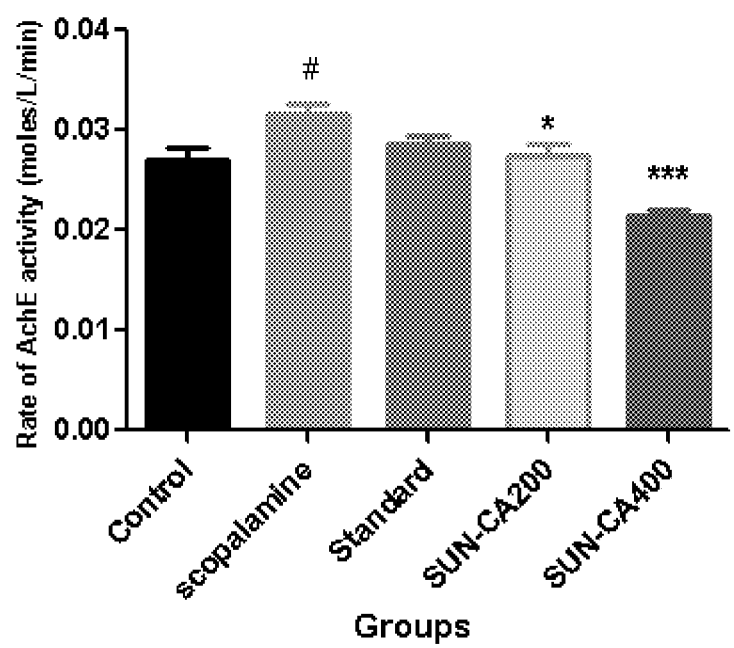
FIG. 8 shows the effect of an embodiment of the inventive composition on brain cholinesterase activity of mice. Values are expressed in terms of SEM±Mean. Data were analyzed by one way ANOVA followed by Dunnett's t test. Number of animals in each group n=8. *Comparison made with control group. # Comparison made with scopolamine group. # $p<0.05$, ***$p<0.001$, *$p<0.05$, ns-non significant.

The composition showed remarkable in brain cholinesterase activity in mice as compared to the respective control groups by using Ellman's kinetic colorimetric method (FIG. 8). The reduction in rate of enzyme activity was highly significant ($p<0.001$) in 400 mg/kg b.w. of composition-treated mice compared to the positive control (scopolamine)

Evaluation of Antioxidant Activity
Superoxide Dismutase Activity (Singh, 2014)

Estimation of superoxide dismutase (SOD) activity in tissue was measured in UV-VIS Spectrophotometer. 0.2 mL of the 10% tissue supernatant samples was placed into each of the reference and test cuvette. Reference cuvette contained 1.5 mL of sodium carbonate buffer (100 mM, pH 10.2) and 1.3 mL of water, while the test cuvette contained 1.5 mL of sodium carbonate buffer (100 mM, pH 10.2) and 1.1 ml of water. The reaction was initiated by adding 0.2 mL of epinephrine (10 mM) in the test cuvette, so that the final volume of reaction mixture would be 3.0 mL. Both the reference and test cuvette were read simultaneously at 480 nm wave length. The gradual increase of OD until attainment of maximum increase of test cuvette against reference cuvette was recorded. One unit of SOD activity is the amount of SOD giving a 50% inhibition.

Catalase Activity (Claiborne, 1985)

A total of 0.1 mL of supernatant was added to a cuvette containing 1.9 mL of 50 mM phosphate buffer (pH 7). The reaction was started by the addition of 1 mL freshly prepared 30 mM $H_2O_2$. The rate of decomposition of $H_2O_2$ was measured spectrophotometrically at 240 nm. Catalase values were expressed as n moles $H_2O_2$ consumed/min/mg protein.

Lipid Peroxidation (Roger-Walker & Edward, 2005)

0.5 mL homogenate and 0.5 mL Tris-HCl (PH—7.4) was taken and incubated at 37° C. for 2 hours; 1 mL 10% TCA (Trichloro acetic acid) was added, centrifuged at 1000×g for 10 min. To 1 mL supernatant, 1 mL of 0.67% TBA (Thiobarbituric acid) was added. The tubes were kept in a boiling water bath for 10 min, cooled the solution and added 1 mL of distilled water then absorbance was measured at 532 nm using UV spectrophotometer.

Determination of Reduced Glutathione (GSH) (Singh, 2014)

Reduced glutathione (GSH) level of tissue was measured in UV-VIS spectrophotometer. Total aliquot was 3 mL, containing 2 mL of 0.6 mM DTNB in 0.2 M Tris-hydrochloric acid buffer (pH 8.0), 0.1 mL of tissue supernatant and 0.9 mL of 0.2 M Tris-hydrochloric acid buffer (pH 8.0). The reference cuvette contained 0.1 mL of 5% Trichloroacetic acid (TCA) instead of tissue sample and after 5 minute, absorbance was read at 412 nm wavelength. Reduced glutathione content of tissue homogenate was expressed as µmole/gm wet tissue.

Figure 9:
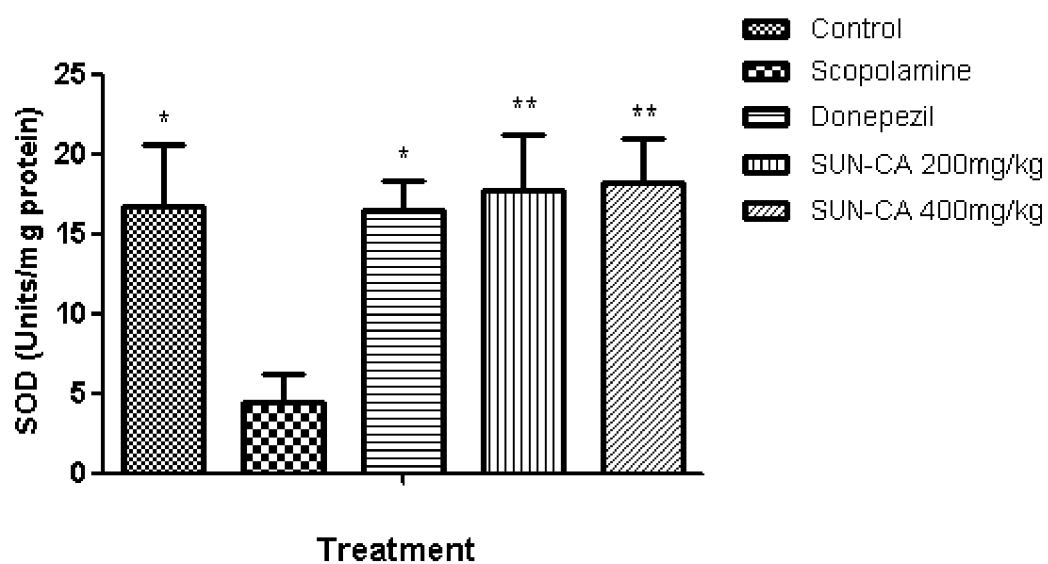
FIG. 9 shows the effect of an embodiment of the inventive composition on superoxide dismutase activity (SOD) in scopolamine treated mice. Values are expressed as mean±SEM. Data were analyzed by one-way ANOVA followed by Dunnet's t test. Number of animals in each group n=8. The data were significant at $p<0.05$ when compared to positive control.
Figure 10:
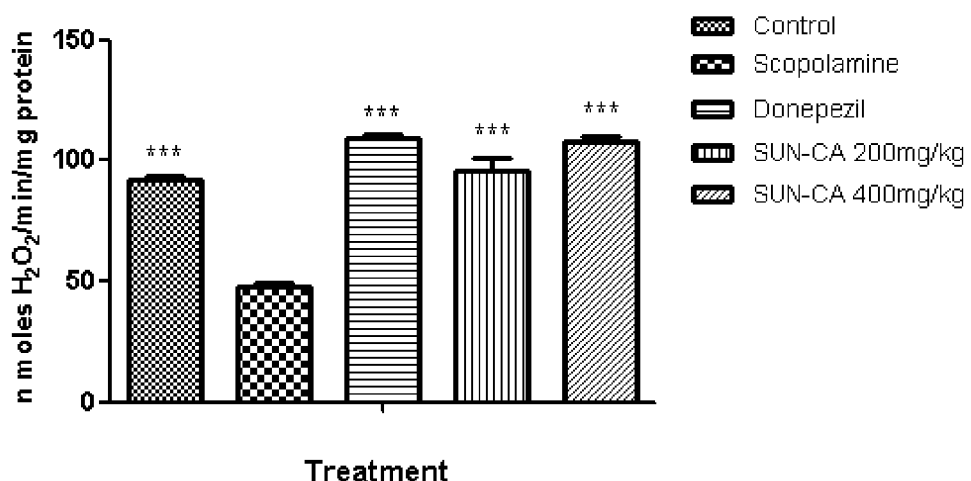
FIG. 10 shows the effect of an embodiment of the inventive composition on catalase activity in scopolamine treated mice. Values are expressed as mean±SEM. Data were analyzed by one way ANOVA followed by Dunnet's t test. Number of animals in each group n=8. The data were significant at $p<0.05$ when compared to positive control.
Figure 11:
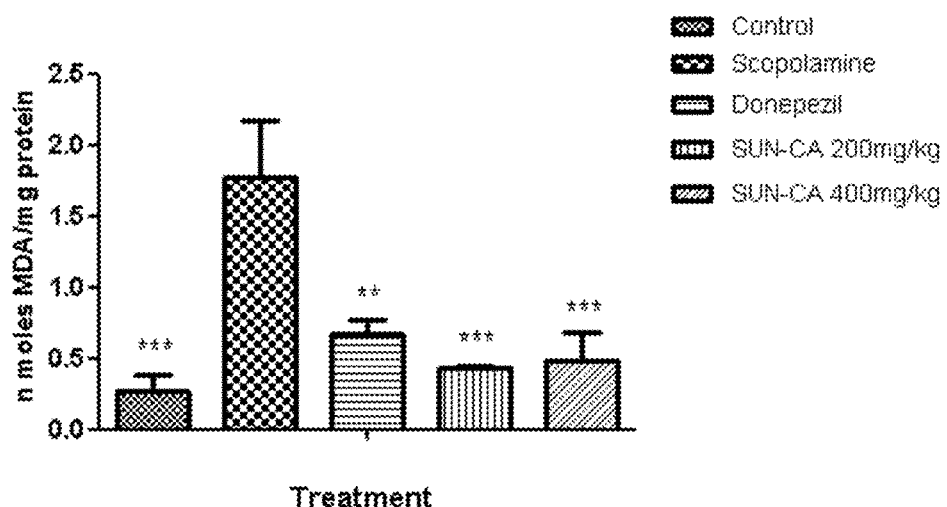
FIG. 11 shows the effect of an embodiment of the inventive composition on melondialdehyde levels (MDA) in scopolamine treated mice. Values are expressed as mean±SEM. Data were analysed by one way ANOVA followed by Dunnet's t test. Number of animals in each group n=8. The data were significant at p<0.05 when compared to positive control.
Figure 12:
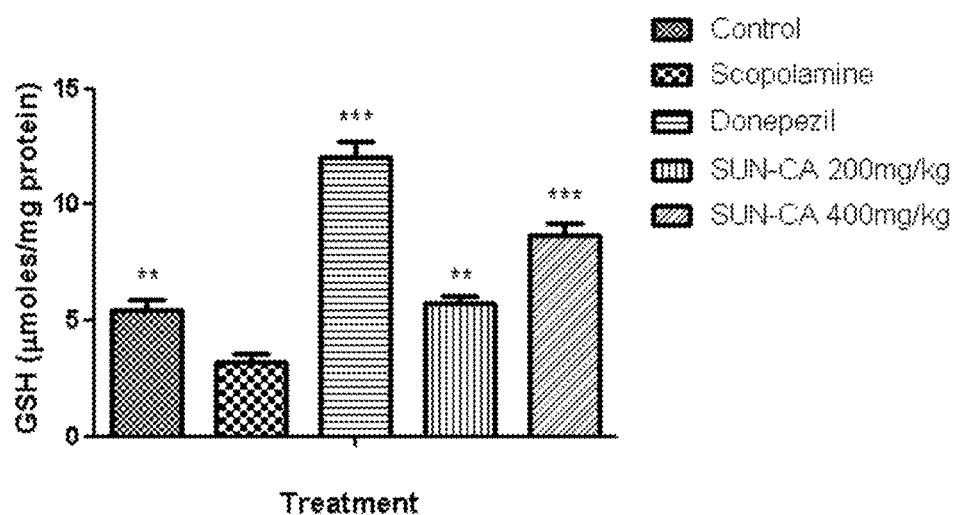
FIG. 12 shows the effect of an embodiment of the inventive composition on reduced GSH levels in scopolamine treated mice. Values are expressed as mean±SEM. Data were analyzed by one way ANOVA followed by Dunnet's t test. Number of animals in each group n=8. The data were significant at p<0.05 when compared to positive control.

The animals treated with the composition (200 and 400 mg/kg b.w.) showed an improvement in their antioxidant defense system. The activity of enzymes such as superoxide dismutase and catalase was reduced in the scopolamine treated mice (FIGS. 9 & 10). Composition treatment restored the level of SOD ($p<0.01$) and catalase activities ($p<0.001$) to the normal levels significantly in mice brain. The protective effect exerted by the composition was comparable to standard Donepezil. The lipid peroxidation as indicated by brain melondialdehyde levels (MDA) was increased in mice treated with scopolamine (FIG. 11). Pretreatment with the composition exhibited protection against lipid peroxidation significantly ($p<0.0001$). The composition was also effective in increasing the reduced glutathione levels (GSH) in brain. Glutathione is an extremely important cell protectant and essential cofactor for many enzymes. There was a dose-dependent increase in the level of reduced GSH and the composition at 400 mg/kg b.w. significantly ($p<0.001$) restored the GSH when compared to scopolamine treated mice (FIG. 9).

Determination of Tau Hyperphosphorylation in Mice Brain

Brain homogenates from control and treated group of mice were estimated for total protein content using Bradford method. Further, the samples were used for the quantitative determination of phosphorylated Tau protein (pTau) using Ms Tau [pS199] ELISA kit, Invitrogen. The absorbance emitted by the individual samples was detected using microplate reader (Thermo Scientific Multiscan EX) at 450 nm. The data were expressed as mean±SEM and analysed by one-way ANOVA followed by Dunnett's multiple comparison test using GraphPad Prism Version 5. Differences were considered significant at $p<0.05$.

Alzheimer's disease is characterized by formation of amyloid plaques and neurofibrillary tangles; the latter composed of hyperphosphorylated and aggregated protein Tau. Tau hyperphosphorylation is one hallmark of Alzheimer's disease pathology. Inhibition of Tau phosphorylation is a possible strategy to improve microtubule stabilization in Alzheimer's disease.

Figure 13:
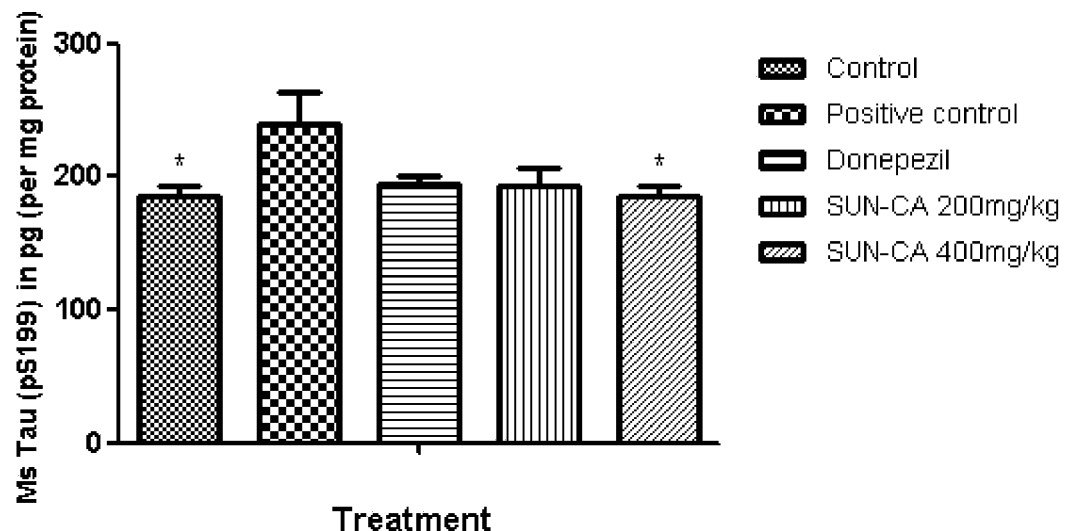
FIG. 13 shows the effect of the administration of an embodiment of the inventive composition on Tau hyperphosphorylation in mice brain homogenates. Data are mean±SEM values of three individual experiments. The values were compared with the control using analysis of variance followed by Dunnet's multiple comparison test. *p<0.05, significant differences from the positive control group.

During this study in mice treated with the composition, there was a noticeable increase in Tau phosphorylation in scopolamine-treated mice (positive control) when compared to the normal group. However, administration of the composition effectively alleviated the hyperphosphorylation status of Tau protein and restored it to normal levels (FIG. 13). Composition treatment at 200 and 400 mg/kg b.w. significantly reduced Tau hyperphosphorylation compared to the positive control ($p<0.05$).

Example 5

This example demonstrates the inventive composition's efficacy in the inhibition of acetylcholinesterase and beta secratase using in silico docking studies.

Beta secratase and acetylcholinesterase are the major therapeutic targets of Alzheimer's pathology. These enzymes are associated with the building up of amyloid beta (Aβ) followed by plaque formation and loss of cholinergic function in Alzheimer's brain.

Structure Based Virtual Screening (In Silico Studies)

In order to study the structure-activity relationship of caffeoylquinic acids in the composition with the enzyme active sites, molecular docking studies were performed.

AutoDock tools were utilized to generate grids, calculate dock score and evaluate the conformers of active principles from the composition bound in the active site of β-secratase and/or acetylcholinesterase as targets for Alzheimer's disease. Automated docking is a graphical user interface. AutoDock 4.2 was employed to get docking and binding scores; which is implemented by Lamarckian genetic algorithm method. The ligand molecules were designed and the structure was analysed using ACD/Chemsketch. The PRODRG server was used to minimize energy of drug compounds and 3D coordinates were prepared. The protein structure files (PDB ID: 2QP8-β-secratase and 2WHQ-Acetylcholinesterase) were taken from PDB and was edited by removing the hetero atoms using Python molecule viewer. The grid map was centred at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Figure 14:
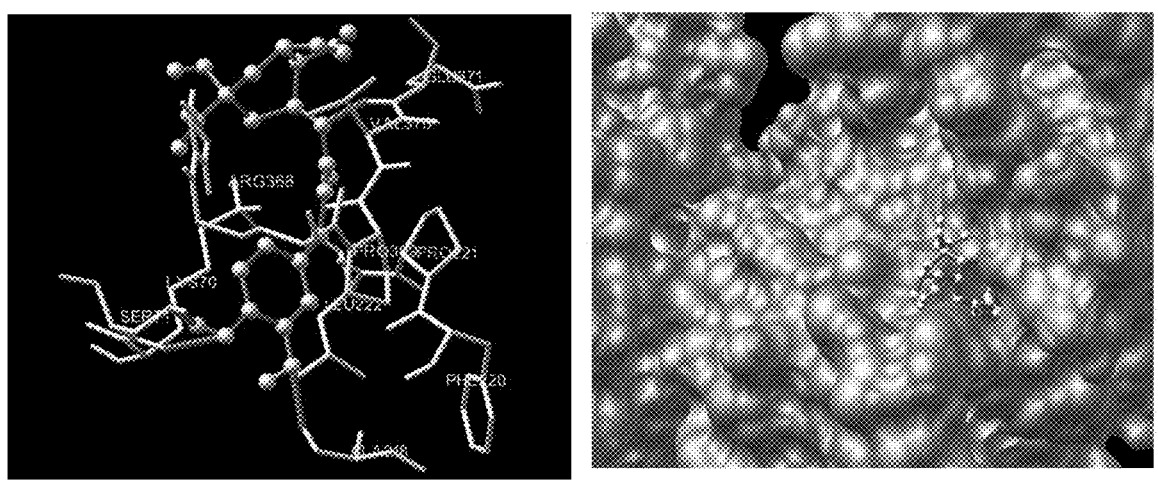
FIG. 14 shows predicted hydrogen bonding interactions (green spheres) between 3-O-caffeoylquinic acid and active residues of β-secratase (B) Binding of 3-O-caffeoylquinic acid with active pocket of β-secratase.
Figure 15:
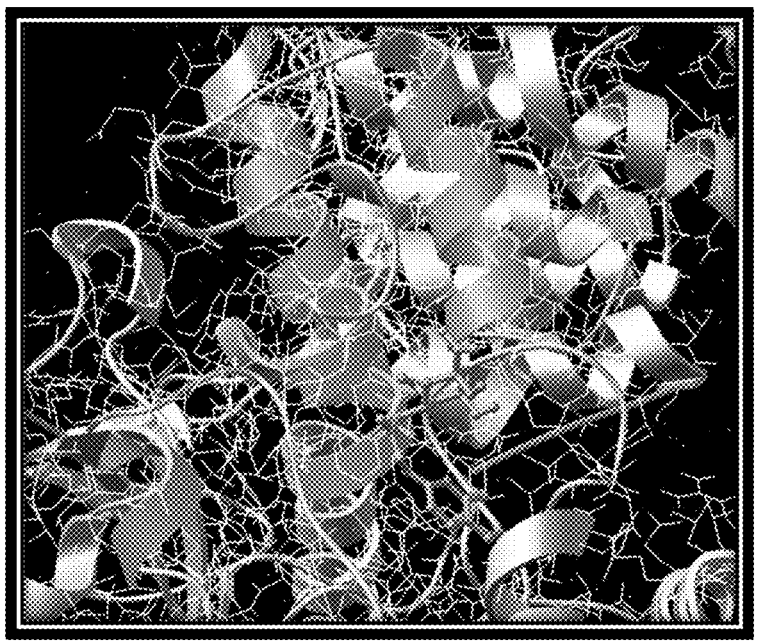
FIG. 15 shows interaction of 5-O-caffeoylquinic acid with acetylcholinesterase.

The docking results revealed compounds with more favorable interactions with the targets and also indicated that some of the compounds present certain structural motifs that could make them form extensive Van der Waals interactions and hydrogen bonding with targets (Table 4 & 5). After comparative docking analysis it was learned that 3-O-Caffeoylquinic acid showed better inhibition of enzyme in comparison to other compounds (binding energy of −7.38 kJ/mol). The molecule interacted with five hydrogen bonds with Ser71, Glu371, Ala218 and Arg 368 residues of β-secratase (FIG. 14). The orientation of chlorogenic acids in the catalytic site of enzyme acetylcholinesterase indicated profound interaction in the form of protein-ligand hydrogen bond formation (FIG. 15). 5-O-caffeoylquinic acid showed better interaction with acetylcholinesterase in comparison to other compounds, with binding energy of −7.12 kJmol$^{-1}$ and forming four hydrogen bonds with active pocket residues; Tyr341, Arg296 and Ser298.

TABLE 4

Molecular docking score of β-secratase with chlorogenic acids of the inventive composition.

| | Thermodynamic parameters | | | | | |
|---|---|---|---|---|---|---|
| Molecule | Binding Energy (KJ/mol) | Ligand Efficiency (KJ/mol) | Inhibitory Constant (µM) | Intermolecular energy KJ/mol | H-bonds | Interactions |
| 3-O-Caffeoylquinic acid | −7.38 | −0.3 | 3.92 | −10.66 | 5 | Ser71, Glu371, Ala218, Arg368 |
| 4-O-Caffeoylquinic acid | −6.54 | −0.26 | 15.99 | −9.82 | 4 | Lys70, Ser71, Glu371, Glu400 |
| 5-O-Caffeoylquinic acid | −6.02 | −0.24 | 38.51 | −9.3 | 5 | Ser71, Gly72, Arg368, Glu371 |
| 3,4-O-Dicaffeoylquinic acid | −6.48 | −0.35 | 5.66 | −8.08 | 3 | Ser71, Lys70, Ala218 |
| 3,5-O-Dicaffeoylquinic acid | −6.18 | −0.17 | 29.5 | −11.25 | 5 | Gly72, Glu371, Arg368, Leu328, Ser71 |
| 4,5-O-Dicaffeoylquinic acid | −7.02 | −0.28 | 85.7 | −9.5 | 4 | Gly72, Ala 218, Arg368 |

TABLE 5

Molecular docking results of Acetylcholinesterase with chlorogenic acids of the inventive composition.

| Phytoconstituent | Binding Energy (KJ/mol) | Ligand Efficiency (KJ/mol) | Inhibitory Constant (µM) | Intermolecular energy KJ/mol | H-bonds | Interactions |
|---|---|---|---|---|---|---|
| 3-O-Caffeoylquinic acid | −7.7 | −0.31 | 2.27 | −10.98 | 2 | Trp286, Ser298 |
| 4-O-Caffeoylquinic acid | −7.09 | −0.28 | 6.38 | −10.37 | 4 | Gly342, Ser298 Glu292, Tyr124 |
| 5-O-Caffeoylquinic acid | −7.12 | −0.28 | 6.09 | −10.4 | 4 | Tyr341, Arg296 Ser298 |
| 3,4-O-Dicaffeoylquinic acid | −8.5 | −0.23 | 585.35 | −13.57 | 3 | Tyr341, Val282 Phe295 |
| 3,5-O-Dicaffeoylquinic acid | −7.02 | −0.19 | 7.12 | −12.09 | 3 | His287, Leu289 Ser298 |
| 4,5-O-Dicaffeoylquinic acid | −5.85 | −0.41 | 6.19 | −11.28 | 2 | Gly342, Ser298 |

The invention claimed is:

1. A method for treating Alzheimer's disease, comprising administering to a subject in need thereof a composition comprising sunflower seed extract obtained from aqueous extraction of sunflower seeds wherein said extract comprises a mixture of chlorogenic acids consisting of 4.1±1.42 w/w % 3-Caffeoylquinic acid (3-CQA), 28±4.65 w/w % 5-Caffeoylquinic acid (5-CQA), 6.5±2.25 w/w % 4-Caffeoylquinic acid (4-CQA), 0.84±0.26 w/w % 3,4-Dicaffeoylquinic acid (3,4-DiCQA), 1.23±0.34 w/w % 3,5-Dicaffeoylquinic acid (3,5-DiCQA), and 1.85±0.42 w/w % 4,5-Dicaffeoylquinic acid (4,5-DiCQA), and wherein administering said composition treats Alzheimer's disease in said subject.

2. The method of claim 1, wherein said composition is administered to said subject at a dosage of about 200-400 mg per kilogram body weight.

3. The method of claim 1, wherein said composition is administered to said subject orally.

4. The method of claim 1, wherein said composition has a DPPH IC50 value of about 38.49 μg/mL in vitro.

5. The method of claim 1, wherein said composition has an acetylcholinesterase IC50 value of about 43 μg/mL in vitro.

6. The method of claim 1, wherein said composition is in a form selected from the group consisting of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, and injectable solution.

7. The method of claim 1, wherein administering said composition to said subject inhibits acetylcholinesterase activity in said subject.

8. The method of claim 1, wherein administering said composition to said subject inhibits Tau phosphorylation in said subject.

9. The method of claim 1, wherein administering said composition to said subject inhibits the formation of amyloid plaques in said subject.

10. The method of claim 1, wherein administering said composition to said subject inhibits the formation of neurofibrillary tangles in said subject.

11. The method of claim 1, wherein administering said composition to said subject inhibits the loss of GSH in said subject.

12. The method of claim 1, wherein administering said composition to said subject increases GSH in said subject.

13. The method of claim 1, wherein said composition comprises an excipient.

* * * * *